US008362083B2

(12) United States Patent
Djordjevic et al.

(10) Patent No.: US 8,362,083 B2
(45) Date of Patent: Jan. 29, 2013

(54) TASTE-MASKED DOCUSATE COMPOSITIONS

(75) Inventors: Jelena Djordjevic, Lynchburg, VA (US); Mohammad Rahman, Lynchburg, VA (US)

(73) Assignee: C.B. Fleet Company Inc., Lynchburg, VA (US)

( * ) Notice: Subject to any disclaimer, the term of this patent is extended or adjusted under 35 U.S.C. 154(b) by 571 days.

(21) Appl. No.: 12/014,616

(22) Filed: Jan. 15, 2008

(65) Prior Publication Data

US 2009/0182052 A1 Jul. 16, 2009

(51) Int. Cl.
*A61K 31/19* (2006.01)
*A01N 37/10* (2006.01)

(52) U.S. Cl. ........................................ 514/569
(58) Field of Classification Search .................. 424/400; 514/569
See application file for complete search history.

(56) References Cited

U.S. PATENT DOCUMENTS

| 4,975,465 | A |   | 12/1990 | Motola et al. |
|---|---|---|---|---|
| 5,154,926 | A |   | 10/1992 | Kawasaki et al. |
| 5,516,524 | A | * | 5/1996 | Kais et al. ................ 424/439 |
| 5,616,621 | A |   | 4/1997 | Popli et al. |
| 5,658,919 | A |   | 8/1997 | Ratnaraj et al. |
| 5,730,997 | A |   | 3/1998 | Lienhop et al. |
| 5,763,449 | A |   | 6/1998 | Anaebonam et al. |
| 5,766,622 | A |   | 6/1998 | Nelson |
| 6,806,256 | B2 |   | 10/2004 | Ulrich et al. |
| 2003/0118654 | A1 | * | 6/2003 | B. Santos et al. ............. 424/486 |
| 2006/0198856 | A1 | * | 9/2006 | Whitehead .................... 424/400 |

FOREIGN PATENT DOCUMENTS

| EP | 0 390 369 A2 | 3/1990 |
|---|---|---|
| EP | 0 441 307 A1 | 2/1991 |

OTHER PUBLICATIONS

Sota Omoigui, M.D. Pain Drug Handbook, Mar. 29, 2003.*
www.medicinehouse.com (Sota Omoigui's Pain Drugs Handbook, 2nd Edition), date of web-page is Mar. 29, 2003.*
Sohi et al., "Taste Masking Technologies in Oral Pharmaceuticals: Recent Developments and Approaches," Drug Development and Industrial Pharmacy, vol. 30, No. 5, pp. 429-448, (2004).
Worthington, "A Matter of Taste," Pharmaceutical Executive, 5 pages, (2001).
BASF Aktiengesellschaft, "Soluble Kollidon® Grades," 16 pages, (2007).
Purdue Products L.P., Material Safety Data Sheet, 7 pages, (2006).

* cited by examiner

*Primary Examiner* — Benjamin Packard
*Assistant Examiner* — Adam C Milligan
(74) *Attorney, Agent, or Firm* — Evan Law Group LLC

(57) ABSTRACT

A taste-masked liquid composition of docusate includes a docusate salt, povidone, a polyether, and water. Additional ingredients in the composition may include thickeners, sweeteners, flavorants, polyols, preservatives, chelating agents and pH adjusters. Such compositions may be used as taste-masked oral compositions of docusate, and may provide therapeutic effects such as stool-softening.

1 Claim, 3 Drawing Sheets

US 8,362,083 B2

TASTE-MASKED DOCUSATE COMPOSITIONS

BACKGROUND

Docusate is the generic name of a surfactant used as a stool softener, which is sold under multiple brand names, for example AQUALAX ®, CALUBE ®, and COLACE ®. Docusate is administered to make stools softer and easier to pass. It is used to treat constipation due to hard stools, in painful anorectal conditions such as hemorrhoids, and for people who should avoid straining during bowel movements. Unfortunately, docusate possesses a strong, unpleasant and bitter taste.

The disagreeable taste of compounds such as docusate is generally not of concern when formulating oral solid dosage forms, because the compound's taste can be easily masked with an exterior coating. The orally administered drug can be provided to the patient in many dosage forms, including solid forms such as capsules, caplets or tablets. Pharmaceutically active agents administered in solid dosage form are usually intended to be swallowed whole.

Many patients, including children, the elderly, and disabled or incapacitated patients, often have trouble swallowing tablets or capsules. In these situations, it is desirable to provide the drug either in a chewable solid form or in a liquid form, such as a solution, syrup, emulsion or suspension. For many patients, a liquid oral dosage form is preferred over a chewable dosage form because of the ease with which a liquid may be swallowed. Additionally, patients may be more inclined to comply with their medication instruction if the dosages are easier to ingest.

Liquid pharmaceutical compositions that include an unpleasant tasting pharmaceutically active agent, such as docusate, usually require the taste to be obscured. Accordingly, a common formulation challenge associated with liquid dosage forms is masking the disagreeable taste of the active ingredient. Unfortunately, commercially available liquid formulations of docusate do not satisfactorily mask its taste, giving rise to difficulties in administration and in assuring patient compliance. Thus, it is desirable to provide a docusate liquid formulation that better masks its taste than those currently available.

SUMMARY

In one aspect, the invention provides a taste-masked liquid composition including from 0.1 w/w % to 2 w/w % of a docusate salt, from 0.5 w/w % to 20 w/w % povidone, from 0.5% to 20% of a polyether, and water.

In another aspect, the invention provides a taste-masked liquid composition including from 0.1 w/w % to 2 w/w % of a docusate salt, from 0.5 w/w % to 20 w/w % povidone, from 0.5 w/w % to 20 w/w % of a polyether, from 2 w/w % to 40 w/w % of a polyol, from 0.005 w/w % to 2 w/w % of a thickener, from 0.05 w/w % to 75 w/w % of a sweetener, from 0.1 w/w % to 4 w/w % of a flavorant, and water.

In yet another aspect, the invention provides a method of softening stool including administering to a subject a taste-masked liquid composition including from 0.1 w/w % to 2 w/w % of a docusate salt, from 0.5 w/w % to 20 w/w % povidone, from 0.5% to 20% of a polyether, and water, in an amount effective to soften the stool of the subject.

In yet another aspect, the invention provides a method of making a taste-masked liquid composition including combining ingredients. The ingredients include a docusate salt, povidone, a polyether and water.

BRIEF DESCRIPTION OF THE DRAWINGS

The invention can be better understood with reference to the following drawings and description.

DEFINITIONS

Figure 1:
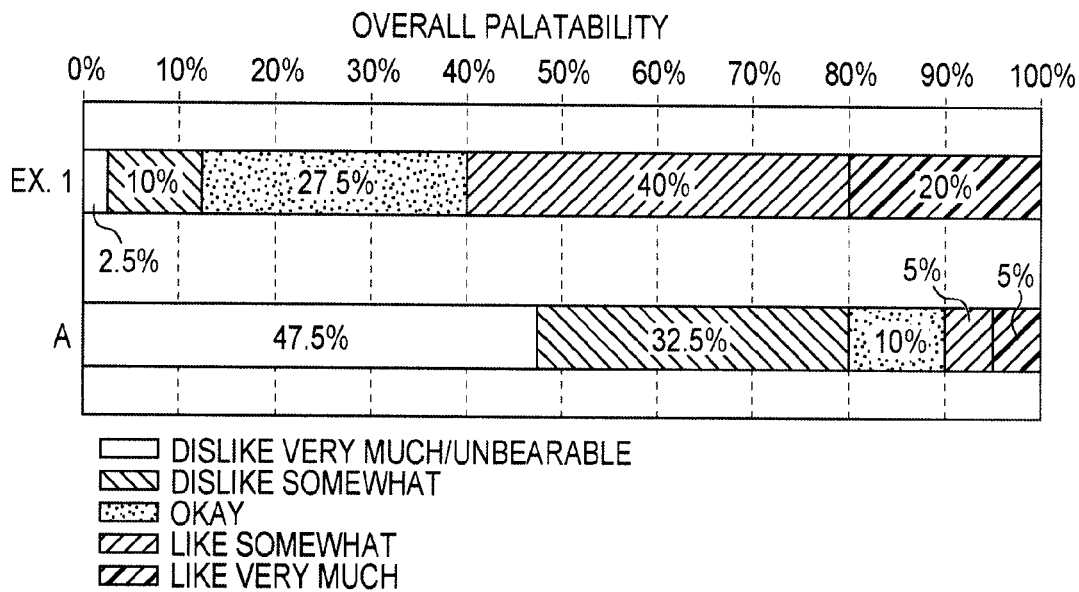
FIG. 1 illustrates graphically the overall palatability ratings of a taste-masked liquid composition of docusate (Example 1) and a commercially available liquid composition of docusate (A), as reported in Table 5.

The following definitions are included to provide a clear and consistent understanding of the specification and claims.

The term "polyether" means a polymer having at least 10 repeating units, and including a plurality of ether (—C—O—C—) groups in the polymer chain. Polyethers include polyethylene glycol (PEG), polypropylene glycol (PPG), methoxypolyethylene glycol, polybutylene glycol, block copolymers of polyethylene oxide (PEO) and polypropylene oxide (PPO) (also known as poloxamers), and block copolymers of butylene oxide and ethylene oxide.

The term "sugar alcohol" means a hydrogenated form of a carbohydrate, in which the aldehyde or ketone group has been reduced to a primary or secondary hydroxyl group. The general formula for a sugar alcohol is $H(HCHO)_{n+1}H$, whereas that of its corresponding carbohydrate is $H(HCHO)_n HCO$. Common sugar alcohols include erythritol, arabitol, xylitol, mannitol, sorbitol, isomalt, maltitol, and lactitol.

The term "polyol" means an alcohol containing multiple hydroxyl groups. Example polyols include propylene glycol and glycerin.

The term "povidone" means polyvinyl pyrrolidone (PVP), a polymerization product of N-vinyl pyrrolidone.

DETAILED DESCRIPTION

The present invention takes advantage of the discovery that aqueous formulations of docusate that include povidone and a polyether have substantially reduced bitter taste and aftertaste, as compared to conventional docusate liquid formulations. Additional ingredients may be present to further improve the palatability of the liquid, and/or to control other properties of the liquid. Such formulations may be used as taste-masked liquid compositions of docusate, and may provide therapeutic effects such as stool-softening.

A taste-masked liquid composition includes a docusate salt, povidone, a polyether, and water. The docusate salt may include a salt of docusate and an alkali metal and/or a salt of docusate and an alkaline earth metal. Examples of docusate salts include lithium docusate, sodium docusate, potassium docusate, magnesium docusate, and calcium docusate. Preferably the docusate salt includes sodium docusate, potassium docusate, or calcium docusate. More preferably, the docusate salt includes sodium docusate. The docusate salt may be present at a concentration of from 0.1 to 2 percent by weight (w/w %). Preferably, the docusate salt is present at a concentration of 0.25 w/w % to 0.35 w/w %.

The polyether may be any polymer having at least 10 repeating units, and including a plurality of ether (-C-0-C-)

groups in the polymer chain. Example polyethers include polyethylene glycol (PEG), polypropylene glycol (PPG), methoxypolyethylene glycol, polybutylene glycol, poloxamers, and block copolymers of butylene oxide and ethylene oxide. Preferred polyethers include polyethylene glycol (PEG) and polypropylene glycol (PPG). Preferably the polyether includes polyethylene glycol. Especially preferred is polyethylene glycol with a molecular weight from 400 to 8000. The polyether may be present at a concentration of 0.5 w/w % to 20 w/w%. Preferably, the polyether is present at a concentration of 1 w/w % to 10 w/w %. More preferably, the concentration of polyether is 3 w/w % to 7 w/w %.

The povidone may contribute to taste-masking, for example, by interacting with the docusate salt and/or by increasing the viscosity of the composition. The povidone preferably has a molecular weight of from 2,000 to 1,500,000 daltons (Da). More preferably, the povidone has a molecular weight of from 28,000 to 54,000 Da. The povidone may be present at a concentration of 0.5 w/w % to 20 w/w %. Preferably, the povidone is present at a concentration of from 1 w/w % to 10 w/w % povidone. More preferably, the concentration of povidone is from 3 w/w % to 7 w/w %. Examples of commercially available povidone include KOLLIDON ® 12 PF, KOLLIDON ® 17 PF, KOLLIDON ® 25, KOLLIDON ® 30, and KOLLIDON ® 90 F (BASF, Ludwigshafen, Germany). Preferred commercially available povidones include KOLLIDON ® 25 and KOLLIDON ® 30.

A taste-masked liquid composition that includes a docusate salt, povidone, a polyether and water may also include at least one additional ingredient. Examples of additional ingredients include thickeners, sweeteners, flavorants, polyols, preservatives, chelating agents, and pH adjusters.

A taste-masked liquid composition may include at least one thickener. A thickener may provide a desired viscosity to the composition. A thickener also may contribute to taste-masking, for example, by increasing the viscosity and/or by interacting with the docusate salt. The thickener may be chosen from those commonly used in oral formulations. Example thickeners include xanthan gum, gum arabica, sodium alginate, methylcellulose, carboxymethylcellulose, hydroxymethylcellulose, hydroxyethylcellulose, hydroxypropylcellulose, hydroxyethylmethylcellulose, hydroxypropylmethylcellulose, carrageenan, guar gum, tragacanth, and pectin. A preferred thickener is xanthan gum. The concentration of thickener may be determined on the basis of the viscosity desired for the composition and/or the amount needed to contribute to taste-masking. Preferably, the concentration of thickener in the composition is from 0.005 w/w % to 2 w/w %.

A taste-masked liquid composition may include at least one sweetener. A sweetener may provide an improvement of the taste of the composition. Example sweeteners include sugars, sugar alcohols, and artificial sweeteners. The concentration of sweetener in a composition may vary according to the potency of the sweetener and the desired flavor for the composition. Preferably, the concentration of the sweetener in the composition is from 0.05 w/w % to 75 w/w %.

Examples of sugar sweeteners include monosaccharides and disaccharides commonly used to sweeten oral compositions. Specific examples include xylose, ribose, sucrose, lactose, maltose, mannose, galactose, glucose, and fructose. If the composition includes a sugar, the concentration of sugar in the composition is preferably from 5 w/w % to 75 w/w %.

Examples of sugar alcohol sweeteners include erythritol, arabitol, xylitol, mannitol, sorbitol, isomalt, maltitol, and lactitol. If the sweetener includes a sugar alcohol, the concentration of sugar alcohol in the composition is preferably from 5 w/w % to 75 w/w %.

Example artificial sweeteners include saccharin, saccharine sodium salt, aspartame, sucralose, neotame, and acesulfame potassium. If the composition includes an artificial sweetener, the concentration of artificial sweetener in the composition is preferably from 0.05 w/w % to 2 w/w % of the composition.

A taste-masked liquid composition may include at least one flavorant. Example flavorants include natural flavors, natural fruit flavors, artificial flavors, and artificial fruit flavors. Preferred flavorants include fruit punch, mint, grape, cherry, strawberry, menthol, and bubble gum. Preferably, the concentration of flavorant in the composition is 0.1 w/w % to 4 w/w %.

A taste-masked liquid composition may include at least one polyol. A polyol may serve as a co-solvent for the composition. Preferred polyols include propylene glycol and glycerin. Preferably, the concentration of polyol in the composition is 2 w/w % to 60 w/w % of the composition.

A taste-masked liquid composition may include at least one preservative. Example preservatives include methyl paraben and propyl paraben. The efficacy of a preservative may be improved by adding a chelating agent, such as disodium edetate. Preferably, the concentration of preservatives and/or chelating agents in the composition is 0.1 w/w % to 0.5%.

Preferably, the pH of the liquid composition is from 4.5 to 6.9. A taste-masked liquid composition may include at least one pH adjuster, which may help control the pH of the liquid composition. Example pH adjusters include buffers that can be used in oral formulations, such as the citric acid—sodium citrate buffer. The pH adjuster also may be an acid or a base.

In one example, a taste-masked liquid composition may include formulation A or B as listed in Table 1.

TABLE 1

Exemplary Formulations of Taste-Masked Liquid Compositions

| Formulation | Concentration (w/w %) | | | | | | |
|---|---|---|---|---|---|---|---|
| | Docusate Salt | Povidone | Polyether | Thickener | Sweetener | Flavorant | Polyol |
| A | 0.1-2 | 0.5-20 | 0.5-20 | 0.005-2 | 0.05-75 | 0.1-4 | 2-40 |
| B | 0.2-1 | 1-10 | 1-10 | 0.01-0.1 | 0.2-50 | 0.5-2 | 5-20 |

In a second example, a taste-masked liquid composition may include formulation C as listed in Table 2.

TABLE 2

Exemplary Formulations of Taste-Masked Liquid Compositions

Concentration (w/w %)

| Formulation | Sodium Docusate | Povidone | Polyethyleneglycol | Thickener | Sweetener | Flavorant | Propylene Glycol |
|---|---|---|---|---|---|---|---|
| C | 0.2-1 | 1-10 | 1-10 | 0.01-0.1 | 0.2-50 | 0.5-2 | 5-20 |

In a third example, a taste-masked liquid composition may include the formulation as listed in Table 3.

TABLE 3

Exemplary Formulation of Taste-Masked Liquid Compositions

| Ingredient | Concentration (w/w %) | Role |
|---|---|---|
| Sodium docusate | 0.29 | Active Ingredient |
| Povidone | 5 | Taste-Masking Agent |
| Polyethylene glycol | 5 | Taste-Masking Agent |
| Propylene glycol | 15 | Co-solvent |
| Xanthan gum | 0.05 | Thickener |
| Sorbitol | 5-25 | Sweetener |
| Xylitol | 5-40 | Sweetener |
| Sucralose | 0.1-1 | Sweetener |
| Fruit punch flavor | 0.1-2 | Flavorant |
| Sodium citrate | 0.05-2 | pH Adjuster |
| Citric acid | 0.05-2 | pH Adjuster |
| Methyl paraben | 0.05-0.3 | Preservative |
| Edetate Disodium | 0.01-1 | Chelating agent |
| Propyl paraben | 0.005-10 | Preservative |

A method of making a taste-masked liquid composition may include combining ingredients, where the ingredients include a docusate salt, povidone, a polyether and water. In one example, the combining ingredients includes combining the polyether and the water to form a first mixture, combining the first mixture and the povidone to form a second mixture, and combining the second mixture and the docusate salt. The combining ingredients may include mixing the combined ingredients. Preferably the combining ingredients is performed without heating.

The ingredients may further include at least one additional ingredient, such as a thickener, a sweetener, a flavorant, a polyol, a preservative, a chelating agent, or a pH adjuster. In one example, the combining ingredients includes forming a first mixture that includes a thickener; forming a second mixture that includes the docusate salt, the povidone, the polyether and the water; and combining the first and second mixtures. In this example, the forming the second mixture may include combining the polyether and the water, adding the povidone, and then adding the docusate salt.

In another example, the combining ingredients includes forming a first mixture that includes a preservative and a thickener; forming a second mixture that includes the docusate salt, the povidone, the polyether, the water and at least one additional ingredient; and combining the first and second mixtures. In this example, the at least one additional ingredient may be a sweetener, a flavorant, a preservative, a chelating agent or a pH adjuster. Also in this example, the first mixture may further include a polyol.

In yet another example, the combining ingredients includes forming a first mixture that includes a polyol, a preservative and a thickener; forming a second mixture that includes the docusate salt, the povidone, the polyether, the water, a sweetener, a preservative, a chelating agent and a pH adjuster; combining the first and second mixtures; and adding a flavorant to the combined mixture. In each of these examples, the combining ingredients may include mixing the combined ingredients. Preferably the combining ingredients and/or the combining first and second mixtures is performed without heating.

EXAMPLES

Example 1

Preparation of a Taste-masked Liquid Composition of Docusate

A taste-masked liquid composition of docusate was prepared with the ingredients set forth in Table 4. A first mixture was prepared by adding the methyl paraben and propyl paraben to the propylene glycol and stirring until dissolved, followed by the addition of the xanthan gum. This first mixture was stirred until it was added to a second mixture.

The second mixture was prepared by first adding, in sequence, the sodium citrate, citric acid and edetate sodium to the purified water, and stirring until dissolved. The polyethylene glycol was then added and stirred until dissolved. The povidone was then added and stirred until dissolved. The following ingredients were then added in sequence, and stirred until dissolved: sodium docusate in PEG 400, sorbitol, and sucralose. Finally, the xylitol was added and stirred until dissolved.

The first mixture was then added to the second mixture with stirring. To this combined mixture was added, in sequence, the FD&C red dye and the fruit punch flavor. This final mixture was stirred to provide a taste-masked liquid composition of docusate.

TABLE 4

Exemplary Formulation of Taste-Masked Liquid Composition

| Ingredient | Concentration (w/w %) | Role |
|---|---|---|
| Purified water, USP | 32.573 | Solvent |
| Sorbitol, 70% Solution, USP | 20.000 | Sweetener |
| Xylitol, FCC | 20.000 | Sweetener |
| Propylene Glycol, USP | 15.000 | Co-solvent |
| Polyethylene Glycol 4600, NF | 5.000 | Taste-masking Agent |
| Povidone, USP | 5.000 | Taste-masking Agent |
| Fruit Punch Flavor, FAII040 | 0.750 | Flavorant |
| Sodium Docusate, USP 50%/ PEG 400, NF 50% | 0.571 | Active Ingredient |
| Sucralose, FCC | 0.500 | Sweetener |
| Sodium Citrate Anhydrous, USP | 0.200 | pH Adjuster |
| Methyl Paraben, NF | 0.180 | Preservative |
| Citric Acid, USP | 0.100 | pH Adjuster |
| Xanthan Gum, NF | 0.050 | Thickener |
| Edetate Disodium, USP | 0.050 | Chelating agent |
| Propyl Paraben, NF | 0.020 | Preservative |
| FD&C Red#3 | 0.006 | Coloring |

Example 2

Taste Evaluation of Liquid Compositions of Docusate

A study was undertaken to compare the taste preference between the taste-masked liquid composition of Example 1 and a commercially available laxative (liquid A). Liquid A was Colace ® Liquid 1% Solution (Purdue Pharma; Stamford, Conn., USA). The ingredients reported for COLACE ® Liquid 1% Solution include 1% sodium docusate, 9% propylene glycol, and undisclosed concentrations of "inactive ingredients" including polyethylene glycol, poloxamer, methyl paraben, propyl paraben, sodium citrate, citric acid, vanillin, D&C red #33, and water. Thus, the liquid composition of Example 1 included a docusate salt, povidone and a polyether; whereas liquid A included a docusate salt and a polyether (polyethylene glycol), but did not include povidone.

The liquid of Example 1 and liquid A were tasted by a panel of 40 subjects, all men and women aged 18 or older. Each subject tasted a sample of the liquid of Example 1, and a sample of liquid A. The order in which the two samples were administered to the subjects was alternated between subjects. After having tried both samples, the subjects completed a questionnaire to evaluate the palatability, bitterness, soapiness, flavor and after-taste, and to note their preference between the two samples.

The subjects rated the palatability of the laxatives as reported below in Table 5. The results of this aspect of the study are shown graphically in FIG. 1. The data establish an overall higher palatability rating for the liquid of Example 1 over liquid A. Specifically, 87.5% of the subjects reported that the liquid of Example 1 either was "okay", or that they liked it somewhat or very much. In contrast, 80% of the subjects reported disliking liquid A somewhat or very much.

TABLE 5

Comparison of Overall Palatability

|  | Example 1 | A |
| --- | --- | --- |
| Dislike very much/unbearable | 2.5% | 47.5% |
| Dislike somewhat | 10% | 32.5% |
| Okay | 27.5% | 10% |
| Like somewhat | 40% | 5% |
| Like very much | 20% | 5% |

Figure 2:
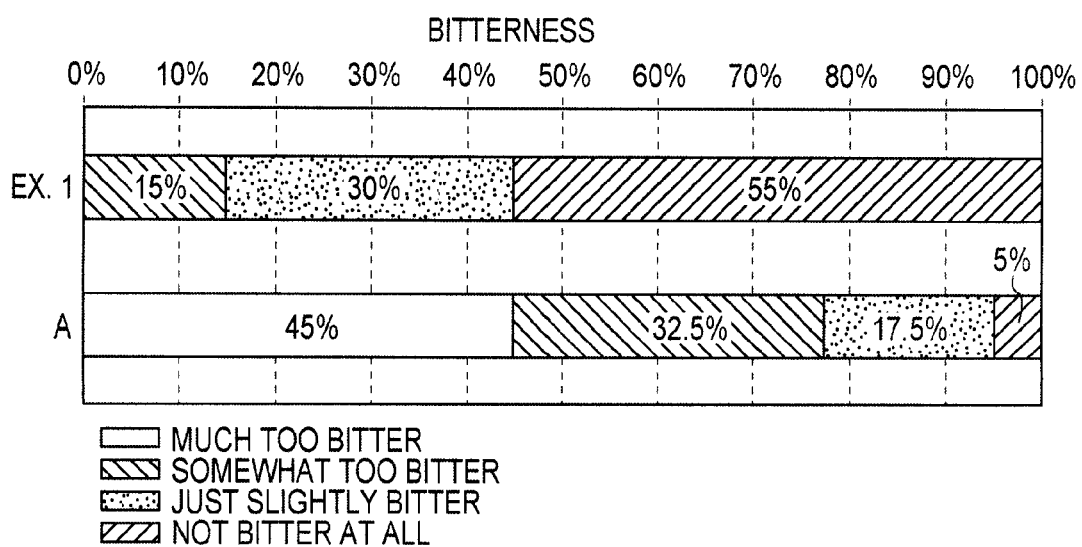
FIG. 2 illustrates graphically the bitterness ratings of the two liquid compositions of docusate, as reported in Table 6.

The liquid of Example 1 was also found to be less bitter than liquid A, as reported below in Table 6 and graphically shown in FIG. 2. Specifically, 85% of the panelists found the liquid of Example 1 to be just slightly bitter or not bitter at all. In contrast, 77.5% of the subjects found liquid A to be somewhat too bitter or much too bitter.

TABLE 6

Comparison of Bitterness

|  | Example 1 | A |
| --- | --- | --- |
| Much too bitter | 0% | 45% |
| Somewhat too bitter | 15% | 32.5% |
| Just slightly bitter | 30% | 17.5% |
| Not bitter at all | 55% | 5% |

Figure 3:
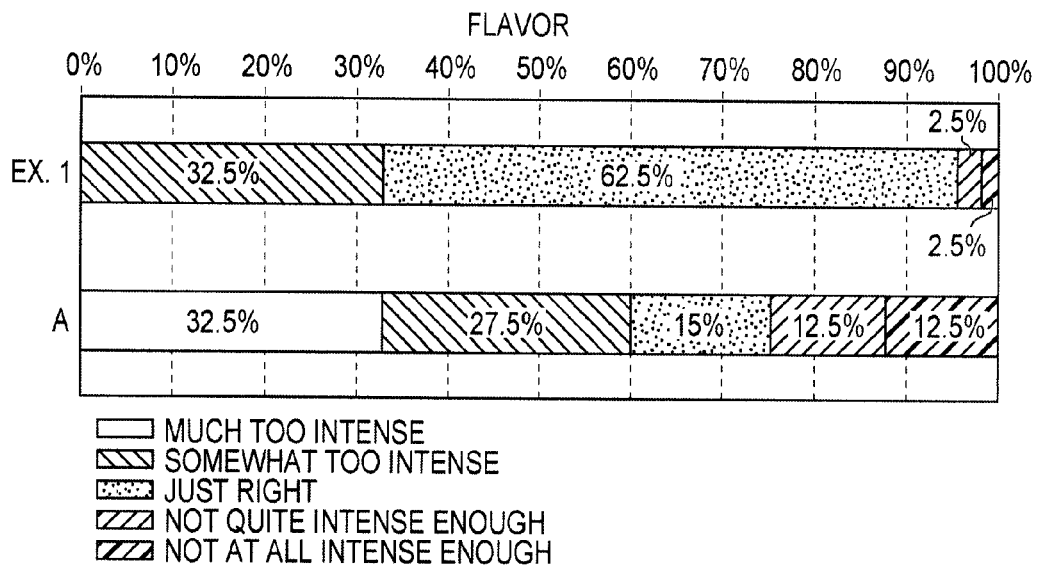
FIG. 3 illustrates graphically the flavor ratings of the two liquid compositions of docusate, as reported in Table 7.

The panel also found the liquid of Example 1 to have a better flavor than liquid A. Specifically, 62.5% of the subjects rated the liquid of Example 1 as having a flavor that was "just right", whereas only 15% of the subjects gave this rating to liquid A. The results are reported below in Table 7 and graphically shown in FIG. 3.

TABLE 7

Comparison of Flavor

|  | Example 1 | A |
| --- | --- | --- |
| Much to intense | 0% | 32.5% |
| Somewhat too intense | 32.5% | 27.5% |
| Just right | 62.5% | 15% |
| Not quite intense enough | 2.5% | 12.5% |
| Not at all intense enough | 2.5% | 12.5% |

Figure 4:
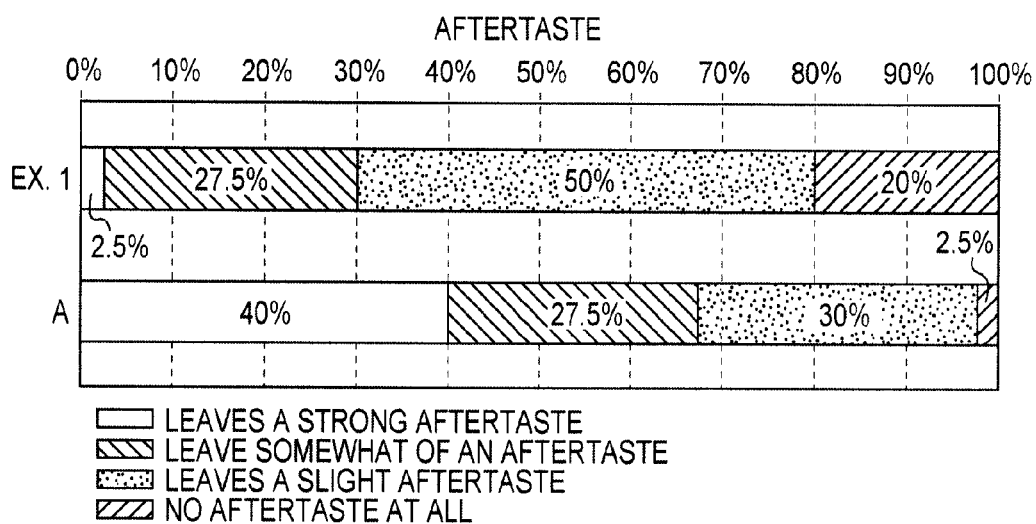
FIG. 4 illustrates graphically the aftertaste ratings of the two liquid compositions of docusate, as reported in Table 8.

More panelists found the liquid of Example 1 to leave less of an aftertaste than liquid A. Specifically, 70% of the subjects reported that the liquid of Example 1 left a slight aftertaste or no aftertaste at all, while only 32.5% of the subjects reported the same about liquid A. The results are reported below in Table 8 and graphically shown in FIG. 4.

TABLE 8

Comparison of Aftertaste

|  | Example 1 | A |
| --- | --- | --- |
| Leaves a strong aftertaste | 2.5% | 40% |
| Leaves somewhat of an aftertaste | 27.5% | 27.5% |
| Leaves a slight aftertaste | 50% | 30% |
| No aftertaste at all | 20% | 2.5% |

Figure 5:
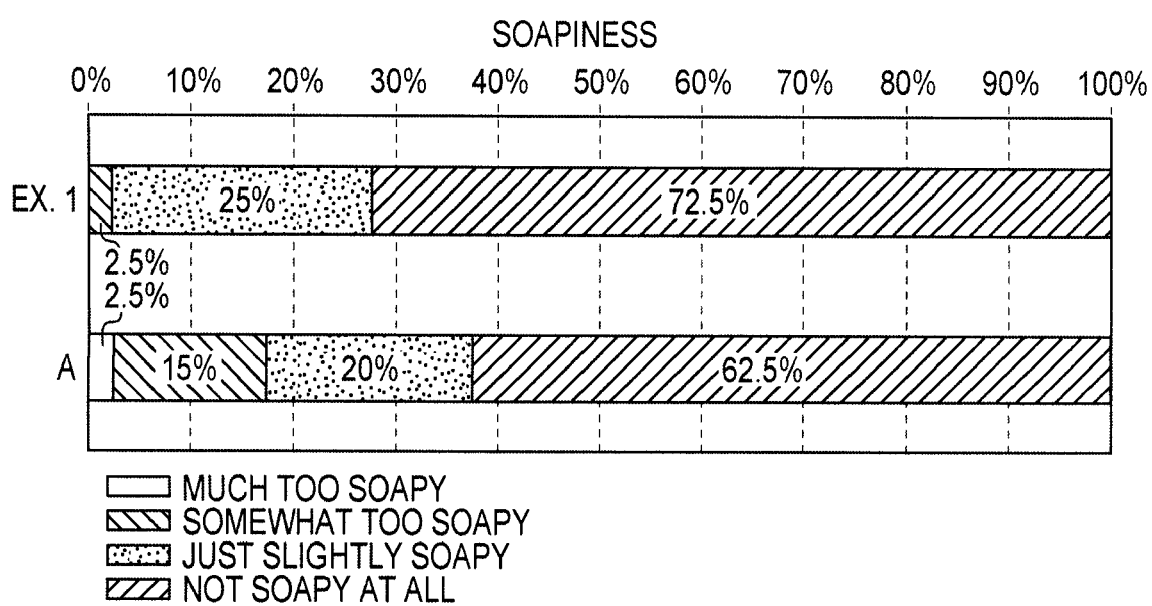
FIG. 5 illustrates graphically the soapiness ratings of the two liquid compositions of docusate, as reported in Table 9.

The subjects also found the liquid of Example 1 to be less soapy than liquid A. Although the differences in this taste parameter are less drastic than the differences for other parameters, the liquid of Example 1 was still rated significantly more favorably than liquid A. The results are reported below in Table 9 and graphically shown in FIG. 5.

TABLE 9

Comparison of Soapiness

|  | Example 1 | A |
| --- | --- | --- |
| Much too soapy | 0% | 2.5% |
| Somewhat too soapy | 2.5% | 15% |
| Just slightly soapy | 25% | 20% |
| Not soapy at all | 72.5% | 62.5% |

In choosing an overall preference between the two docusate liquid compositions, an overwhelming majority of the subjects preferred the liquid of Example 1. Specifically, 92.5% of the subjects preferred the liquid of Example 1.

The taste-masking performance of the combination of povidone and a polyether in a liquid composition of docusate was surprising and unexpected. The liquid of Example 1 drastically outperformed the conventional liquid composition of docusate, both in overall preference and in individual taste parameters.

While various embodiments of the invention have been described, it will be apparent to those of ordinary skill in the art that other embodiments and implementations are possible within the scope of the invention. Accordingly, the invention is not to be restricted except in light of the attached claims and their equivalents.

References

Sohi H. et al., Drug Development and Industrial Pharmacy 30 (2004) 429-448.
Worthington J., A Matter of Taste, Pharmaceutical Executive, April 2001.
Kawasaki Y. et al., U.S. Pat. No. 5,154,926.
Popli S. D. et al., U.S. Pat. No. 5,616,621.
Ulrich S. A. et al., U.S. Pat. No. 6,806,256.
Anaebonam A. O., U.S. Pat. No. 5,763,449.
Lienhop K. S., U.S. Pat. No. 5,730,997.
Ratnaraj, S. M., U.S. Pat. No. 5,658,919.
Nelson S. L., U.S. Pat. No. 5,766,622.
Motola S. et al., European Patent No. 0390369.
Kawasaki Y. et al., European Patent No. 0441307.

What is claimed is:

1. A taste-masked liquid composition, comprising:
   0.29 w/w % sodium docusate;
   5 w/w % povidone;
   5 w/w % polyethyleneglycol;
   15 w/w % propylene glycol;
   0.05 w/w % xanthan gum;
   a sweetener comprising sorbitol, xylitol, and sucralose, the sorbitol accounting for 5 w/w % to 25 w/w % of the composition, the xylitol accounting for about 5 w/w % to 40 w/w % of the composition, and the sucralose accounting for 0.1 w/w % to 1 w/w % of the composition;
   a flavorant comprising fruit punch flavor, the fruit punch flavor accounting for 0.1 w/w % to 2 w/w % of the composition;
   a pH adjuster comprising sodium citrate and citric acid, the sodium citrate accounting for 0.05 w/w % to 2 w/w % of the composition, and the citric acid accounting for 0.05 w/w % to 2 w/w % of the composition;
   a preservative comprising methyl paraben, edetate disodium and propyl paraben, the methyl paraben accounting for 0.05 w/w % to 0.3 w/w % of the composition, and the propyl paraben accounting for 0.005 w/w % to 1 w/w % of the composition; and
   a chelating agent comprising edentate disodium, the edentate disodium accounting for 0.01 w/w % to 1 w/w % of the composition,
   wherein the sodium docusate is the sole pharmaceutically active agent.

* * * * *

UNITED STATES PATENT AND TRADEMARK OFFICE
CERTIFICATE OF CORRECTION

| | |
|---|---|
| PATENT NO. | : 8,362,083 B2 |
| APPLICATION NO. | : 12/014616 |
| DATED | : January 29, 2013 |
| INVENTOR(S) | : Jelena Djordjevic and Mohammad Rahman |

Page 1 of 1

It is certified that error appears in the above-identified patent and that said Letters Patent is hereby corrected as shown below:

Title Page

Item (73) Assignee:
Please delete "C.B. Fleet Company Inc." and insert --C. B. Fleet Company Incorporated--.

Signed and Sealed this
Seventeenth Day of February, 2015

Michelle K. Lee
*Deputy Director of the United States Patent and Trademark Office*